United States Patent [19]
Smith et al.

[11] Patent Number: 6,133,300
[45] Date of Patent: Oct. 17, 2000

[54] ANTIMICROBIAL MIXTURES OF 1,3-BIS (HYDROXYMETHYL)-5,5-DIMETHYLHYDANTOIN AND 1,2-BENZISOTHIAZOLIN-3-ONE

[75] Inventors: Roger Errol Smith, Neshanic Station, N.J.; Eric S. Bensaid, Stamford, Conn.

[73] Assignee: Troy Technology Corporation, Inc., Wilmington, Del.

[21] Appl. No.: 09/419,167

[22] Filed: Oct. 15, 1999

[51] Int. Cl.⁷ .......................... A01N 43/50; A01N 43/80; C09D 5/16; C09D 5/18
[52] U.S. Cl. ....................... 514/373; 514/389; 106/18.32; 106/18.33
[58] Field of Search ..................................... 514/373, 389; 106/18.32, 18.33

[56] References Cited

U.S. PATENT DOCUMENTS

| | | | |
|---|---|---|---|
| 4,844,891 | 7/1989 | Rosen et al. | 424/76.4 |
| 5,112,871 | 5/1992 | Austin | 514/727 |
| 5,125,967 | 6/1992 | Morpeth et al. | 106/18.22 |
| 5,160,666 | 11/1992 | Lindner et al. | 252/402 |
| 5,594,018 | 1/1997 | Austin | 514/313 |

*Primary Examiner*—Allen J. Robinson
*Attorney, Agent, or Firm*—Robert F. Tavares

[57] ABSTRACT

This invention is directed to a broad spectrum antimicrobial composition which comprises a mixture of 1,2-benzisothiazolin-3-one, or a salt thereof, (BIT) and 1,3-bis (hydroxymethyl)-5,5-dimethylhydantoin (DMH), said mixture provided in an amount to protect a substrate from attack by one or more bacterial organisms. The composition can be used broadly in industrial systems and more particularly with substrates such as paints, coatings, stucco, concrete, stone, cementaceous surfaces, wood, caulking, sealants, textiles, leather, wood, preservatives, metal working fluids, drilling muds, clay slurries, glazes, optical brightness, carpet backing, pigments and as a preservative for other aqueous and wet state products, and the like.

20 Claims, No Drawings

ANTIMICROBIAL MIXTURES OF 1,3-BIS (HYDROXYMETHYL)-5,5-DIMETHYLHYDANTOIN AND 1,2-BENZISOTHIAZOLIN-3-ONE

BACKGROUND OF THE INVENTION

1. Field of the Invention

The present invention pertains to antimicrobial compositions suitable for use in the protection of paints, metal working fluids, process water, mineral slurries, leather, inks, carpet backings, asphalt emulsions, adhesives, dispersions and other wet state industrial products from spoilage resulting from the growth of microorganisms, especially bacteria. The antimicrobial composition comprises mixtures of 1,2-benzisothiazolin-3-one and 1,3-bis(hydroxymethyl)-5,5-dimethylhydantoin which, in combination, demonstrate synergistic activity in controlling microorganisms and is an especially useful combination in protecting paint.

2. Description of the Background

Substrates of all types and water-containing compositions and formulations, when exposed to common environmental conditions, are prone to attack, spoilage and various kinds of destruction by a variety of species of microorganisms including fungi, yeast, algae, bacteria and protozoa. As a result, there has always been a great need for effective and economical means to protect, for extended periods of time, commercial compositions and formulations from the deterioration and destruction caused by such microorganisms.

Materials which need protection against such microorganisms include, for example, materials such as paints and other coating formulations, surfactants, proteins, starch-based compositions, inks, emulsions and resins, stucco, concrete, stone, wood adhesives, caulking, sealants, leather, and spin finishes. Other important commercial materials that are prone to degradation by microorganisims are polymer dispersions or aqueous latex paints containing polyvinyl alcohol, polyacrylates or vinylpolymers, thickener solutions containing cellulose derivatives, clay and manual suspensions and metal working fluids. All are prone to degradation by the action of objectionable microorganisms which can spoil and significantly impair the usefulness of such compositions. Such degradation may produce, inter alia, changes in pH values, gas formation, discoloration, the formation of objectionable odors, and/or changes in rheological properties.

Antimicrobials are also important during the processing of materials. For example, animal skins are susceptible to attack by microorganisms both prior to and after the tanning process. Prior to the tanning process, bactericides are used in the brine solutions to prevent bacteria from damaging the hide grain. After the tanning process, the so called wet blue hides are subject to fungal attack during storage or transport and fungicides are used to inhibit this fungal growth. Antimicrobials can also be used in the fat liquors and leather finishing products to prevent the growth of bacteria, fungi and yeast.

A great deal of effort has gone into developing a wide variety of materials which, to various degrees, are effective in retarding or preventing the growth of, and the accompanying destruction caused by, such microorganisms in a variety of circumstances. Such antimicrobial compounds included halogenated compounds, organometallic compounds, quaternary ammonium compounds, phenolics, metallic salts, heterocyclic amines, formaldehyde donors, organosulfur compounds and the like.

No single organic antimicrobial compound is able to provide protection against all microorganisms or is suitable for all applications. In addition to such limitations concerning efficacy, other limitations may restrict the usefulness of certain antimicrobials. For example the stability, physical properties, toxicological profile, regulatory considerations, economic considerations or environmental concerns may render a particular ingredient unsuitable for a particular use. There is a need, therefore, to constantly develop new combinations that will offer broad spectrum protection in a variety of applications.

A judicious choice of combinations may provide a way to maximize benefits while at the same time minimize problems. Ideally, a combination wherein the antimicrobial activity is enhanced while the less desirable properties are suppressed can provide an unexpectedly superior product. The task is to find such combinations that will provide protection against a wide variety of problem microorganisms, will not adversely affect the product to be protected, will maintain its integrity for an extended period of time, and will not have any adverse effect on health or the environment.

The antimicrobial 1,3-bis(hydroxymethyl)-5,5-dimethylhydantoin has found wide use in a number of applications as an effective broad spectrum antimicrobial preservative. The antimicrobial 1,2-benzisothiazolin-3-one, including salts thereof, have also found wide use in a number of applications as effective broad spectrum antimicrobial preservatives. What has not been known heretofore is that these two bacteriocides provide a strong synergistic effect when used in combination.

SUMMARY OF THE INVENTION

The present invention is directed to antimicrobial mixtures comprising 1,2-benzisothiazolin-3-one (BIT), including salts thereof, and 1,3-bis(hydroxymethyl)-5,5-dimethylhydantoin (DMH). These mixtures provide unexpected and surprising synergistic results which were not obtained when these ingredients were used separately. The present invention is also directed to a method for inhibiting microbial growth which comprises contacting the microbial growth with a mixture of 1,3-bis(hydroxymethyl)-5,5-dimethylhydantoin (DMH) and 1,2-benzisothiazolin-3-one (BIT), including salts thereof.

DETAILED DESCRIPTION OF THE INVENTION

The first component of the antimicrobial combination of this invention is 1,3-bis(hydroxymethyl)-5,5-dimethylhydantoin (DMH). The second component of the antimicrobial combination of this invention is the commercially available 1,2-benzisothiazolin-3-one (BIT), including salts thereof. It should be understood that hereafter the use of the term BIT is intended to encompass the 1,2-benzisothiazolin-3-one per se and its salts. Suitable salts of BIT include all alkali metal salts of BIT, in particular the lithium, sodium, or potassium salts, or ammonium salts of BIT. The lithium and sodium salts of BIT are preferred.

In the preferred embodiments of this invention it has been found that synergistic results appear across all blends. The practical range of BIT to DMH runs from 1:9 to 9:1 with 1:4 to 4:1 being preferred and 1:3 to 3:2 being especially preferred. The optimal ratio is 2:3.

It is a surprising and unexpected finding of this invention that the BIT and DMH are especially effective in complementing one another by combining strengths and minimizing weaknesses in an unexpected and unobvious way. For example, one advantage of DMH is its effectiveness against

*Psuedonmonas aeruginosa* and other types of resistant bacteria. A weakness is that its effect does not last as long as is desirable. BIT's strength, on the other hand, is its long persisting activity. Its weakness appears to be a relative weakness against certain bacteria such as *Psuedomonas aeruginosa*. The combined antimicrobial mixture, however, provides a high level of activity over a prolonged period of time, providing the strengths of both ingredients while minimizing the weaknesses of each and doing so in a manner and degree that could not be anticipated. It is this type of complimentary activity that allows one to use less biocide in combination to achieve a desired effect that cannot be achieved with either separately.

In accordance with the invention, the combined antimicrobial constituents can be included in a final formulation for use in such end use applications as paints, coatings, metal working fluids, inks, asphalt emulsions, stucco, adhesives, mineral slurries, leather, dispersions, emulsions, aqueous materials, optical brighteners, oil field chemicals, inks, caulking, sealants, textiles, and the like, in a broad range from about 0.004% to 2.0% active concentration. Such compositions can be prepared from highly concentrated compositions of the active ingredients by appropriate dilution. The optimum useful range is about 0.01% to 1.0% of combined products in the final formulations for such end use systems. With the use of such modified formulations in end use systems, it is possible to protect aqueous substrates for extended periods of time against growth from microorganisms.

Compositions of the present invention will generally be formulated by mixing or dispersing the active ingredients in a selected proportion with a liquid vehicle for dissolving or suspending the active components. The vehicle may contain a diluent, an emulsifier and a wetting-agent. Expected uses of the biocidal compositions include the protection of aqueous based paints and coatings, adhesives, joint cements, sealants, caulks, printing inks, metal working fluids, polymer emulsions, pigment dispersions, aqueous industrial products, lubricants, caulkings, and the like. The synergistic combinations of the DMH and BIT may be provided as liquid mixtures, as wettable powders, dispersions, or in any other suitable product type which is desirable. In this regard, the composition of the present invention can be provided as a ready-for-use product in the form of aqueous solutions and dispersions, oil solutions and dispersions, emulsions, or as a concentrate.

Useful solvents for the DMH and BIT combination are several glycol ethers and esters like propylene glycol n-butyl ether, propylene glycol tert-butyl ether, 2-(2-methoxymethylethoxy)-tripropylene glycol methyl ether, propylene glycol methyl ether, dipropyleneglycol methyl ether, tripropylenelene glycol methyl ether, propylene glycol n-butyl ether and the esters of the previously mentioned compounds. Other useful solvents are n-methyl pyrrolidone, n-pentyl propionate and dibasic esters of several dicarboxylic acids and mixtures thereof.

The preferred solvents for these products are propylene glycol n-butyl ether, 1-methoxy-2-propanol, and the dibasic isobutyl ester blend of succinic, glutaric and adipic acids.

When preparing formulations of the present invention for specific applications, the composition also will likely be provided with adjuvants conventionally employed in compositions intended for such applications such as organic binding agents, additional antimicrobials, auxiliary solvents, processing additives, fixatives, plasticizers, UV-stabilizers or stability enhancers, water soluble or water insoluble dyes, color pigments, siccatives, corrosion inhibitors, antisettlement agents, anti-skinning agents and the like.

According to the present invention, substrates are protected from contamination by microorganisms simply by treating said substrate with a composition of the present invention. Such treating may involve mixing the composition with the substrate, coating or otherwise contacting the substrate with the composition and the like.

A surprising aspect of the invention was found to be that mixtures of DMH and BIT are especially efficacious and synergistic in controlling the bacteria *Pseudomonas aeruginosa* and *Bacillus subtilis*. These organisms are generally present in air, soil and water, and appear on most surfaces when moisture is present. Consequently, these two bacteria are a major commercial problem.

The present invention is directed inter alia to synergistic mixtures of BIT and DMH. A synergistic effect is generally regarded as the response of a mixture of two or more components that is greater than the sum of the response of the individual components. A mathematical approach for assessing synergy, as reported by F. C. Kull, P. C. Elisman, H. D. Sylwestrowicz and P. K. Mayer, in *Applied Microbiology*, 9.538 (1961) can be applied to binary mixtures using the following equation:

$$\text{Synergistic Index } (SI) = Q_a/Q_A + Q_b/Q_B$$

where:

$Q_a$=the quantity of component A used in a mixture that gives the desired effect (such as no target organism growth), $Q_A$=the quantity of component A which when used alone gives the desired effect, $Q_b$=the quantity of component B used in a mixture that gives the desired effect, and $Q_B$=The quantity of component B which when used alone gives the desired effect.

If the SI for a compositions is less than one (<1), that composition exhibits synergistic behavior.

The following examples are presented to illustrate and explain the invention. Unless otherwise indicated, all references to parts and percentages are based on weight.

EXAMPLES

Example 1

Illustrative of Synergistic Activity

Minimum Inhibitory Concentrations of the biocides DMH and BIT, alone and in combination, were determined against pure cultures of *Escherichia coli, Bacillus subtilis*, and *Pseudomonas aeruginosa* grown in nutrient medium. These bacteria were selected for their individual characteristics making them especially resistant to individual biocides in industrial applications. *E. coli* is a fast growing representative of the Gram negative class of bacteria frequently found in cases of industrial bacterial spoilage. *B. subtillis* is an especially troubling bacterium as it produces spores which are not effectively controlled by 1,2-benzisothiazolin-3-one or other biocides. *P. aeruginosa* is a spoilage bacterium that is notoriously resistant to many types of biocides.

The Minimum Inhibitory Concentrations (MIC) of the antimicrobial components and mixtures in this test were determined by the broth dilution techniques described by Block (S. S. Block, Disinfection, Sterilization, and Preservation $_4$th ed., pg 1035, Lea and Gebiger, Philadelphia, 1991):

Test cultures were prepared as overnight cultures grown in m-TGE broth (Difco #0750-15-5). The cultures were adjusted to roughly $10^6$ colony forming units per ml, by comparison to a 0.5 McFacland standard, and then further diluted 1:200 in sterile m-TGE broth.

A dilution series of biocide, in m-TGE broth, was prepared in screw-capped tubes. Using a sterile pipette, 1 ml of diluted bacterial culture was added to each tube in the dilution series. Tubes were then incubated at 29° C. for 16 to 18 hours, removed from the incubator, mixed by a vortex mixer, and returned to incubation for an additional 2 hours. Control tubes without biocide were included.

The lowest concentration of biocide that resulted in complete inhibition of visible bacteria growth was recorded as the MIC for the biocide or mixture.

The data was analyzed according to the method of Kull et. al. mentioned earlier and showed a strong synergistic response by the blended biocides as compared to their unblended parent components. The synergistic effect is shown by the reduction of the MICs by the combined biocides as compared to the MICs of the individual components as evidenced by the calculated synergistic indices for the combinations. The DMH used was Troysan 395 (1,3-Bis(hydroxymethyl)-5,5-dimethylhydantoin, 30.0%, plus Hydroxymethyl-5,5-dimethylhydantoin; 7.5%). The BIT used was Troysan 586 (1,2-benzisothiazolin-3-one). The mixtures were 1:1, 2:3 and 3:2 mixture of DMH and BIT. The results are provided in Table 1. The Synergistic Indicies (SI) are in parenthesis following the appropriate MIC values.

TABLE 1

Minimum Inhibitory Concentration (MIC) and
Synergistic Index of BIT and DMH mixtures

| TEST MATERIAL | B. subtilis | P. aeruginosa | E. coli |
|---|---|---|---|
| BIT | 170 | 320 | 170 |
| DMH | 500 | 1120 | 250 |
| BIT:DMH 50:50 | 90 (SI = .35) | 340 (SI = .64) | 110 (SI = .54) |
| BIT + DMH 60:40 | — | — | 70 (SI-.36) |
| BIT + DMH 40:60 | 50 (SI = .18) | 320 (SI = .57) | — |

Test results actually show that unexpected synergistic results in inhibition and growth reduction were obtained with the test mixtures as compared with effects to be expected or predicted from the individual ingredients when tested against these same bacteria.

EXAMPLE 2

Test Results in Paint

In this example an acrylic, vinyl acrylic white house paint was used as the test medium. The composition of the paint is shown in Table 2.

TABLE 2

FORMULATION OF ACRYLIC, VINYL ACRYLIC
WHITE HOUSE PAINT

| No | Ingredient | Supplier | % W/W |
|---|---|---|---|
| 1 | Natrosol 250 MHR 100% | Aqualon | 0.3 |
| 2 | Propylene glycol | | 1.7 |
| 3 | Tamol 850 (30%) | Rohm & Haas | 0.9 |
| 4 | KTPP | FMC | 0.12 |
| 5 | Nopco NXZ | Hüls | 0.1 |
| 6 | Triton CF-10 | Union Carbide | 0.21 |
| 7 | Water | | 13.44 |
| 8 | Titanium dioxide | Kerr McGee | 14.5 |
| 9 | Minex 4 | Uniman | 15.7 |
| 10 | Silica (Silver Bond B) | Uniman | 6.4 |
| 11 | Attagel | Engelhard | 0.85 |
| 12 | UCAR 379 | Union Carbide | 6.31 |
| 13 | Rhoplex AC-264 (60.5%) | Rohm & Haas | 25.2 |
| 14 | Nopco NXZ | Hüls | 0.17 |
| 15 | Propylene glycol | | 4.1 |
| 16 | Natrosol 250 MHR(2.5%) | | 10.0 |
| | TOTAL | | 100.00 |

*Pseudomonas aeruginsoa* was selected as the test bacteria because it is an important spoilage organism for paint and other industrial products and is also known to be difficult to control for most biocides. The test bacteria were grown on Difco m-TGE agar medium adjusted to alkaline pH levels (pH 8.1) similar to that of the test paint. This period of pH adaptation assured that the test bacteria would grow in the test paint.

Bactericide blends were selected for evaluation using a simplex experimental design. In this design the proportion of each ingredient varied between 0 to 20% as active ingredient As a constraint, the sum of the proportions of all active ingredients equaled 20%. Some of the bactericide blends were duplicated as a measurement of experimental error. Table 2 shows the experimental blends tested and survival rate of test bacteria.

Biocide mixtures were prepared in batches of 100 grams. Each biocide was weighted to provide the correct amount on an active basis. The biocides were combined by stirring them into a sample of test paint so that each test formulation was 20% actives and 80% paint. Each was stirred to achieve a homogeneous mixture.

To run the optimization, test paints were prepared for each of the biocide blends. Each of the test paint blends was dosed by ading the biocide mixtures prepared above at the rate of 0.80% based on the weight of the paint treated. Biocide blends were incorporated into the test paint by stirring.

Test paints were inoculated with bacteria by adding 2% by weight of test paint that contained *Pseudomonas aeruginosa* bacteria. The inoculum had greater than $10^8$ viable bacteria per gram. The bacteria were incorporated into the test paints by stirring. Inoculated test paints were placed in a constant temperature (29° C.) bacterial incubator for 168 hours. At the end of the incubation, bacteria numbers in each test paint were counted using standard dilution plate count procedures.

Results showed that numbers of viable bacteria count ranged from 4 to 700 per gram of test paint. (Synergistic activity is evident when the bacteria count for mixtures is compared with that of the pure components)

TABLE 2

| TEST BLEND # | % BIT | % DMH | BACTERIAL COUNT |
|---|---|---|---|
| 1 | 0.10 | 0.10 | 41 |
| 2 | 0.05 | 0.15 | 4 |
| 3 | 0.20 | 0.00 | 410 |

TABLE 2-continued

| TEST BLEND # | % BIT | % DMH | BACTERIAL COUNT |
|---|---|---|---|
| 4 | 0.00 | 0.20 | 120 |
| 5 | 0.10 | 0.10 | 52 |
| 6 | 0.20 | 0.00 | 700 |
| 7 | 0.00 | 0.20 | 320 |
| 8 | 0.15 | 0.05 | 59 |

All statistical procedures are described by Snee (Design and Analysis of Mixture Experiments, J. of Quality Technology, Vol 3, No. 4, October 1971). Polynomial mixture models were used to predict the responses of the dependent variables to changes in the concentrations of DMH and BIT.

Statistical analysis showed a significant and highly reliable fit for the data. The correlation coefficient for the model was 0.84 described in Steel and Torrie, Principles and Procedures of Statistics, McGraw-Hill, 1960.

Graphical analysis of the master equation predicted the optimum blend of biocides to be 2 parts BIT to 3 parts DMH. All calculations are based on the concentration of active ingredient.

While the invention has been particularly described in terms of specific embodiments, those skilled in the art will understand in view of the present disclosure that numerous variations and modifications upon the invention are now enabled, which variations and modifications are not to be regarded as a departure from the spirit and scope of the invention. Accordingly, the invention is to be broadly construed and limited only by the scope and spirit of the following claims.

We claim:

1. A biocidal composition comprising a synergistically biocidally effective amount of a mixture of 1,3-bis(hydroxymethyl)-5,5-dimethylhydantoin and 1,2-benzisothiazolin-3-one or a salt thereof.

2. The composition of claim 1 wherein 1,3-bis(hydroxymethyl)-5,5-dimethylhydantoin and the 1,2-benzisothiazolin-3-one, or a salt thereof, are present in a proportion of from about 1 part 1,3-bis(hydroxymethyl)-5,5-dimethylhydantoin to 9 parts 1,2-benzisothiazolin-3-one, or a salt thereof, to about 9 parts of 1,3-bis(hydroxymethyl)-5,5-dimethylhydantoin to 1 part 1,2-benzisothiazolin-3-one, or a salt thereof.

3. A composition of claim 2 wherein 1,2-benzisothiazolin-3-one is present.

4. The composition of claim 2 wherein the sodium or lithium salt of 1,2-benzisothiazolin-3-one is present.

5. The composition of claim 2 wherein 1,3-bis(hydroxymethyl)-5,5-dimethylhydantoin and the 1,2-benzisothiazolin-3-one, or a salt thereof, are present in a proportion of from about 1 part 1,3-bis(hydroxymethyl)-5,5-dimethylhydantoin to 4 parts 1,2-benzisothiazolin-3-one, or a salt thereof, to about 4 parts 1,3-bis(hydroxymethyl)-5,5-dimethylhydantoin to 1 part 1,2-benzisothiazolin-3-one, or a salt thereof.

6. A composition of claim 5 wherein 1,2-benzisothiazolin-3-one is present.

7. The composition of claim 5 wherein the sodium or lithium salt of 1,2-benzisothiazolin-3-one is present.

8. The composition of claim 6 wherein the mixture of 1,2-benzisothiazolin-3-one and 1,3-bis(hydroxymethyl)-5,5-dimethylhydantoin are present in a proportion of about 2 parts 1,2-benzisothiazolin-3-one to 3 parts 1,3-bis(hydroxymethyl)-5,5-dimethylhydantoin.

9. An aqueous wet state composition of the type subject to microbial contamination which has been preserved by adding thereto a synergistically effective amount of a biocidal composition comprising a mixture of 1,3-bis(hydroxymethyl)-5,5-dimethylhydantoin and 1,2-benzisothiazolin-3-one, or a salt thereof, wherein 1,3-bis(hydroxymethyl)-5,5-dimethylhydantoin and the 1,2-benzisothiazolin-3-one, or a salt thereof, are present in a proportion of from about 1 part 1,3-bis(hydroxymethyl)-5,5-dimethylhydantoin to 9 parts 1,2-benzisothiazolin-3-one, or a salt thereof, to about 9 parts of 1,3-bis(hydroxymethyl)-5,5-dimethylhydantoin to 1 part 1,2-benzisothiazolin-3-one, or a salt thereof.

10. The wet state composition of claim 9 which is a paint.

11. The composition of claim 9 wherein 1,2-benzisothiazolin-3-one is present.

12. The composition of claim 9 wherein the sodium or lithium salt of 1,2-benzisothiazolin-3-one is present.

13. The composition of claim 9 wherein 1,3-bis(hydroxymethyl)-5,5-dimethylhydantoin and the 1,2-benzisothiazolin-3-one, or a salt thereof, are present in a proportion of from about 1 part 1,3-bis(hydroxymethyl)-5,5-dimethylhydantoin to 4 parts 1,2-benzisothiazolin-3-one, or a salt thereof, to about 4 parts 1,3-bis(hydroxymethyl)-5,5-dimethylhydantoin to 1 part 1,2-benzisothiazolin-3-one, or a salt thereof.

14. The composition of claim 13 which is a paint.

15. A composition of claim 13 wherein 1,2-benzisothiazolin-3-one is present.

16. The composition of claim 13 wherein the sodium or lithium salt of 1,2-benzisothizolin-3-one is present.

17. The composition of claim 9 wherein the mixture is present from about 0.004% to about 5.0%.

18. The composition of claim 15 wherein the mixture is present from about 0.004% to about 5.0%.

19. The composition of claim 18 which is a paint.

20. A method for protecting a substrate from microbial infestation which comprises treating said substrate with a synergistically effective amount of a biocidal composition comprising a mixture of 1,2-benzisothiazolin-3-one, or a salt thereof, and 1,3-bis(hydroxymethyl)-5,5-dimethylhydantoin wherein 1,3-bis(hydroxymethyl)-5,5-dimethylhydantoin and the 1,2-benzisothiazolin-3-one, or a salt thereof, are present in a proportion of from about 1 part 1,3-bis(hydroxymethyl)-5,5-dimethylhydantoin to 9 parts 1,2-benzisothiazolin-3-one, or a salt thereof, to about 9 parts of 1,3-bis(hydroxymethyl)-5,5-dimethylhydantoin to 1 part 1,2-benzisothiazolin-3-one, or a salt thereof.

* * * * *